(12) United States Patent
Anderskewitz et al.

(10) Patent No.: US 6,288,277 B1
(45) Date of Patent: Sep. 11, 2001

(54) BENZYLAMINE AND PHENYLETHYLAMINE DERIVATIVES, PROCESSES FOR PREPARING THE SAME AND THEIR USE AS MEDICAMENTS

(75) Inventors: Ralf Anderskewitz, Bingen; Kurt Schromm, Ingelheim; Ernst-Otto Renth, Kiel; Franz Birke, Ingelheim; Hans Michael Jennewein, Wiesbaden; Christopher John Montague Meade, Bingen, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/423,160
(22) PCT Filed: Nov. 5, 1998
(86) PCT No.: PCT/EP98/02530
§ 371 Date: Apr. 3, 2000
§ 102(e) Date: Apr. 3, 2000
(87) PCT Pub. No.: WO98/49131
PCT Pub. Date: Nov. 5, 1998

(30) Foreign Application Priority Data

Apr. 30, 1997 (DE) .............................. 197 18 334

(51) Int. Cl.$^7$ .................................. C07C 211/00
(52) U.S. Cl. .......... 564/384; 564/385; 564/389; 564/165; 560/27; 560/42; 562/451; 514/329; 514/539; 514/570; 514/620; 514/655; 546/245

(58) Field of Search ................................ 564/384, 385, 564/389, 165; 560/42, 27; 562/451; 514/655, 539, 620, 329, 570, 568; 546/245

(56) References Cited

U.S. PATENT DOCUMENTS 5,686,496 11/1997 Anderskewitz et al. .
5,731,332 3/1998 Anderskewitz et al. .

Primary Examiner—Samuel Barts
(74) Attorney, Agent, or Firm—R. P. Raymond; T. X. Witkowski; M-E M. Devlin

(57) ABSTRACT

The present invention relates to new phenylamine derivatives, processes for preparing them and their use as pharmaceutical compositions. The phenylamines according to the invention correspond to the general formula I

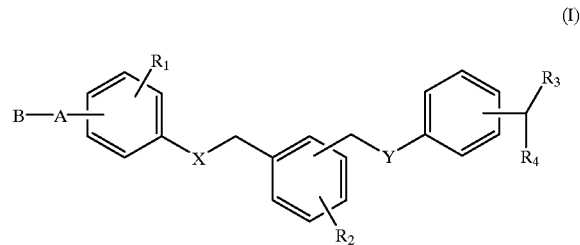

12 Claims, No Drawings

BENZYLAMINE AND PHENYLETHYLAMINE DERIVATIVES, PROCESSES FOR PREPARING THE SAME AND THEIR USE AS MEDICAMENTS

The present invention relates to new benzylamine derivatives and phenylethylamine derivatives, processes for preparing them and their use as pharmaceutical compositions.

Benzyl- or phenylethylamine derivatives according to the invention correspond to general formula I

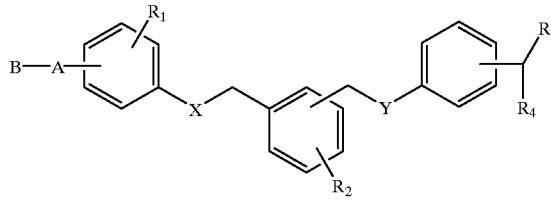

wherein
X denotes O, NH, N(CH$_3$), CH$_2$;
Y denotes O, NH, N(CH$_3$), CH$_2$;
R$_1$ denotes H, F, Cl, Br, I, C$_{1-6}$-alkyl, OH, O—C$_{1-6}$-alkyl, CF$_3$;
R$_2$ denotes H, F, Cl, Br, I, C$_{1-6}$-alkyl, OH, O—C$_{1-6}$-alkyl, CF$_3$;
R$_3$ denotes H, NH$_2$, NHCOR$_5$;
R$_4$ denotes H, CH$_2$NH$_2$, CH$_2$NHCOR$_5$;
R$_5$ denotes H, C$_{1-6}$-alkyl, phenyl, O—(C$_{1-6}$-alkyl), whilst the phenyl ring may be substituted up to twice by: F, Cl, Br, I, R$_a$, OR$_a$, CF$_3$,
R$_a$ denotes H, C$_{1-6}$-alkyl;
A denotes CR$_6$R$_7$, CO, SO$_x$, O;
x denotes an integer 0, 1 or 2;
R$_6$ denotes H, C$_{1-4}$-alkyl, C$_{3-6}$-cycloalkyl, —(CH$_2$)$_y$COOR$_8$, CF$_3$, —(CH$_2$)$_y$OR$_8$, OR$_8$;
y denotes an integer 0, 1, 2, 3 or 4;
R$_7$ denotes H, C$_{1-4}$-alkyl, C$_{3-6}$-cycloalkyl, —(CH$_2$)$_z$COOR$_8$, —(CH$_2$)$_z$OR$_8$, CF$_3$;
z denotes an integer 0, 1, 2, 3 or 4, whilst R$_6$ and R$_7$ together may optionally form a C$_{3-6}$-cycloalkyl ring;
R$_8$ denotes H, C$_{1-6}$-alkyl;
B denotes C$_{1-6}$-alkyl, CONR$_9$R$_{10}$, Ar, and, if A represents —C(CH$_3$)$_2$: CH$_2$NR$_9$R$_{10}$, CH$_2$NR$_9$COR$_{11}$;
Ar denotes phenyl, naphthyl, thienyl, pyridyl—optionally substituted up to twice with R$_{12}$,
R$_9$ denotes H, C$_{1-6}$-alkyl;
R$_{10}$ denotes H, C$_{1-6}$-alkyl, whilst R$_9$ and R$_{10}$ together with the nitrogen atom may form a ring having 3 to 7 carbon atoms;
R$_{11}$ denotes H, C$_{1-6}$-alkyl, —O—(C$_{1-6}$-alkyl), phenyl;
R$_{12}$ denotes H, C$_{1-6}$-alkyl, O—(C$_{1-6}$-alkyl), F, Cl, Br, I, R$_a$, CF$_3$, CHF$_2$, C(CH$_3$)$_2$-phenylene-OH, COOR$_a$, CONR$_a$R$_b$, OR$_c$;
R$_a$ denotes H, C$_{1-6}$-alkyl;
R$_b$ denotes H, C$_{1-6}$-alkyl, whilst optionally R$_a$ and R$_b$ together with the nitrogen atom may form a ring having 3 to 7 carbon atoms;
R$_c$ denotes H, C$_{1-6}$-alkyl, COOR$_d$, COR$_d$ or a group of formula

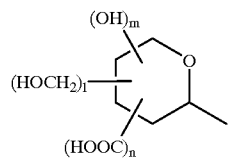

l, m, n denote an integer 0, 1, 2, 3 or 4 whilst l+m+n≦4;
R$_d$ denotes C$_{1-6}$-alkyl, phenyl,
optionally in the form of the individual optical isomers, mixtures of the individual enantiomers or racemates and in the form of the free bases or the corresponding acid addition salts with pharmacologically acceptable acids—with the proviso that R$_3$ and R$_4$ together cannot denote hydrogen.

Preferred compounds of general formula I are those wherein
X denotes O;
Y denotes O;
R$_1$ denotes H, F, Cl, Br, I, C$_{1-6}$-alkyl, OH, O—C$_{1-6}$-alkyl, CF$_3$;
R$_2$ denotes H, F, Cl, Br, I, C$_{1-6}$-alkyl, OH, O—C$_{1-6}$-alkyl, CF$_3$;
R$_3$ denotes NH$_2$;
R$_4$ denotes H;
A denotes CR$_6$R$_7$, O;
R$_6$ denotes H, C$_{1-4}$-alkyl, CF$_3$;
R$_7$ denotes H, C$_{1-4}$-alkyl, CF$_3$, whilst R$_6$ and R$_7$ together may optionally form a C$_{3-6}$-cycloalkyl ring;
B denotes phenyl, optionally substituted up to twice with F, Cl, Br, I, R$_a$, OR$_c$, CF$_3$;
R$_a$ denotes H, C$_{1-6}$-alkyl;
R$_c$ denotes H, C$_{1-6}$-alkyl, COOR$_d$, COR$_d$ or a group of formula

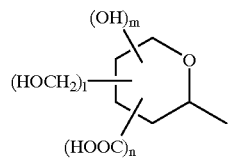

l, m, n denote an integer 0, 1, 2, 3 or 4 whilst l+m+n≦4;
R$_d$ denotes C$_{1-6}$-alkyl, phenyl
optionally in the form of the individual optical isomers, mixtures of the individual enantiomers or racemates and in the form of the free bases or the corresponding acid addition salts with pharmacologically acceptable acids.

Unless otherwise stated in specific instances, the general definitions are used in the following sense:

C$_{1-4}$-alkyl, C$_{1-6}$-alkyl or C$_{1-8}$-alkyl generally represents a branched or unbranched hydrocarbon group with 1 to 4 or 6 or 8 carbon atom(s), which may optionally be substituted by one or more halogen atom(s)—preferably fluorine—which may be identical to or different from one another. The following hydrocarbon groups are mentioned by way of example: methyl, ethyl, propyl, 1-methylethyl (isopropyl), n-butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylproypyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2,-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Unless otherwise stated, lower alkyl groups with 1 to 4 carbon atoms, such as methyl; ethyl, propyl, iso-propyl, n-butyl, 1-methylpropyl, 2-methylpropyl or 1,1-dimethylethyl, are preferred.

It has been found that the compounds of formula I according to the invention are characterised by their multiplicity of uses in the therapeutic field and by their oral efficacy. Special mention should be made of those possible uses in which the $LTB_4$-receptor-antagonistic properties play a part. The following deserve particular mention:

arthritis, asthma, chronic obstructive lung diseases, such as chronic bronchitis, psoriasis, ulcerative colitis, gastropathy or enteropathy induced by non-steroidal antiinflammatories, cystic fibrosis, Alzheimer's disease, shock, reperfusion damage/ischaemias, atherosclerosis and multiple sclerosis.

The new compounds can also be used to treat diseases or conditions wherein the passage of cells from the blood through the vascular endothelium into the tissues is of importance (e.g. metastasis) or diseases and conditions wherein the combination of $LTB_4$ or another molecule (such as 12-HETE) with the $LTB_4$-receptor influences cell proliferation (e.g. chronic myeloid leukaemia).

The new compounds may also be used in conjunction with other active substances, e.g. those which are used for the same indications, or for example with antiallergics, secretolytics, $\beta_2$-adrenergics, inhaled steroids, antihistamines and/or PAF-antagonists, NSAIDs and glucocorticoids. The substances may be administered topically, orally, transdermally, nasally, by parenteral route or by inhalation.

Pharmacological and biochemical testing of the activity ratios may be carried out using tests as described, for example, in WO 93/16036, pages 15 to 17—to which reference is hereby made.

The therapeutic or prophylactic dose depends, not only on the potency of the individual compounds and the body weight of the patient, but also on the nature and gravity of the disease. For oral administration the dose is between 1 and 500 mg, preferably between 20 and 250 mg. For inhalation the dose is between about 0.5 and 25, preferably between about 2 and 20 mg of active substance.

Inhalable solutions generally contain between about 0.5 and 5% active substance. The new compounds may be administered in conventional preparations, e.g. as plain or coated tablets, capsules, lozenges, powders, granules, solutions, emulsions, syrups, inhalable aerosols, ointments and suppositories.

The examples which follow illustrate some possible formulations for the preparations:

EXAMPLES OF FORMULATIONS

| 1. Tablets | |
|---|---|
| Composition: | |
| Active substance according to the invention | 20 parts by weight |
| Stearic acid | 6 parts by weight |
| Glucose | 474 parts by weight |

The ingredients are processed in the usual way to obtain tablets weighing 500 mg. If desired the content of active substance may be increased or reduced and the quantity of glucose reduced or increased accordingly.

| 2. Suppositories | |
|---|---|
| Composition: | |
| active substance according to the invention | 100 parts by weight |
| powdered lactose | 45 parts by weight |
| cocoa butter | 1555 parts by weight |

The ingredients are processed in the usual way to obtain suppositories weighing 1.7 g.

3. Inhalable Powder

Micronised powdered active substance (compound of formula I; particle size about 0.5 to 7 $\mu$m) optionally with the addition of micronised lactose is packed into hard gelatin capsules in a quantity of 5 mg. The powder is inhaled from conventional inhalers, e.g. according to DE-A 33 45 722, to which we hereby refer.

The compounds according to the invention may be produced starting from compounds known from the prior art using, inter alia, the processes described in the Examples which follow. Various other embodiments of the processes will become apparent to the skilled person from the present specification. However, it is expressly pointed out that these Examples and the associated description are provided solely in order to illustrate the invention and not to restrict it.

EXAMPLES OF SYNTHESIS

Compounds according to the invention may be obtained from chloromethyl compounds of formula (II) or corresponding compounds with nucleofugic leaving groups such as halogen, alkyl or aryl sulphonate, with aminoalkylphenols (III)

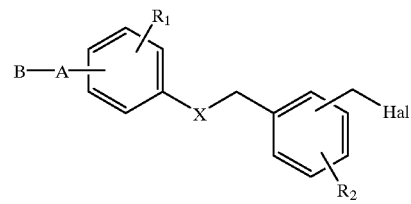

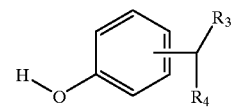

by reaction with basic adjuvants such as hydroxides, alkoxides, carbonates in polar solvents such as DMF, acetonitrile or ethanol or mixtures thereof (Example 2). (R1 to R4, and A, B and X being defined as hereinbefore; Hal primarily represents halogen or an alkyl or aryl sulphonate group).

Compounds of the invention may also be prepared from the corresponding nitrile compounds by reduction of compounds of formula (IV), e.g. at temperatures of 0–100° C., either by catalytic hydrogenation in alcoholic solvents such as methanol, ethanol or higher alcohols, or DMF or water, with catalysts such as Raney nickel, Pd/C or platinum, and pressures of 760 Torr upwards, or by using hydride reagents—particularly complex hydrides—such as $NaBH_4$, $Ca(BH_4)_2$, $LiAlH_4$ and other aluminium or boron hydrides (Example 1).

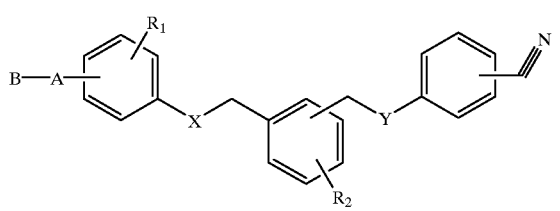

(wherein $R_1$, $R_2$, A, B, X and Y are as hereinbefore defined).

EXAMPLE 1

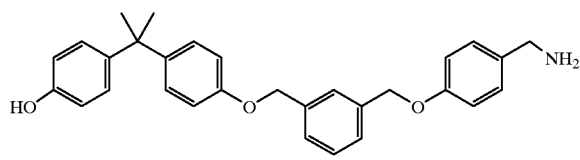

4-[[3-[[4-[1-(4-Hydroxyphenyl)-1-methylethyl]phenoxy]methyl]phenyl]methoxy]-benzylamine hydrochloride 2 g of 4-[[3-[[4-[1-(4-hydroxyphenyl)-1-Methylethyl]phenoxy]methyl]phenyl]methoxy]-benzonitrile were dissolved in 50 ml methanol and Raney nickel was added. The mixture was hydrogenated for 6 hours at ambient temperature under normal pressure. The catalyst was removed by suction filtering and the solvent was distilled off. The residue was taken up in methanol, acidified with ethanolic hydrochloric acid and the product was chromatographed over silica gel with dichloromethane/methanol 1:1. After crystallisation with ethyl acetate/ether, 0.5 g of product was obtained as the hydrochloride with a melting point of 161–162° C.

EXAMPLE 2

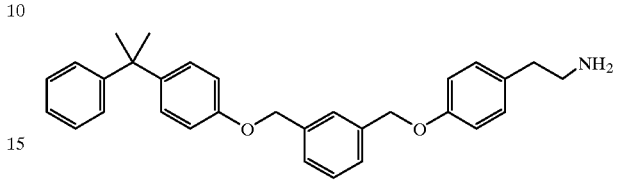

2-[4-[[3-[[4-[1-phenyl-1-methylethyl]phenoxy]methyl]phenyl]methoxy]]-ethylamine hydrochloride 1.15 g of 4-aminoethyl-phenol were dissolved in 15 ml of methanol and 1.5 g of sodium methoxide was added as a 30% solution in methanol. The solvent was distilled off and the residue was added to a solution of 2.93 g of 3-(4-(2-phenylpropyl)-phenoxymethyl)-benzylchloride in 25 ml of acetonitrile. The mixture was stirred for 3 hours at 60–70° C. The solvent was distilled off, the residue was acidified with alcoholic hydrochloric acid and the product was precipitated with ether. The substance was chromatographed with dichloromethane/methanol 7:3. Yield: 1 g, melting point 145° C.

| Salt | | melting point (° C.) | /$K_i$ (nM) |
|---|---|---|---|
| hydrochloride | | 161–162 | 15.7 |
| hydrochloride | | 133–134 | 16.2 |
| hydrochloride | | 175 | 13.8 |

-continued
| Salt | melting point (° C.) | /$K_i$ (nM) |
|---|---|---|
| 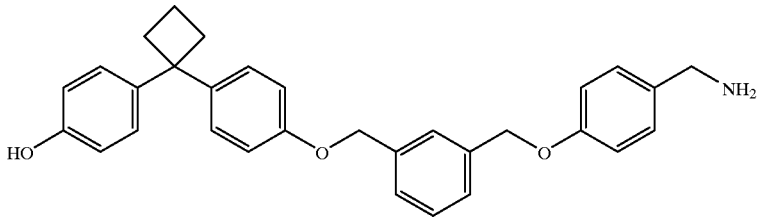 | | |
| hydrochloride | 117–119 | 11.1 |
| 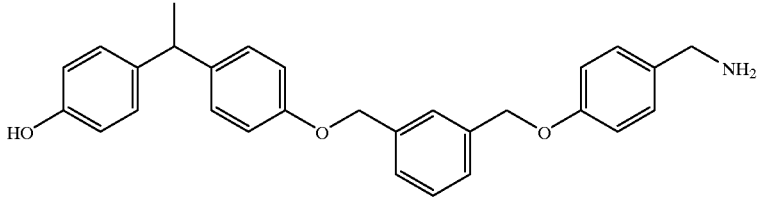 | | |
| hydrochloride | 138–140 | 21.5 |
| 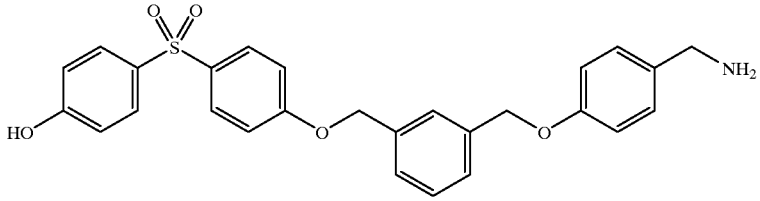 | | |
| hydrochloride | 122–124 | 1.9 |
| 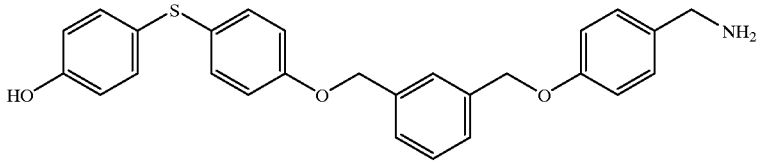 | | |
| hydrochloride | 177–181 | 28.7 |
| 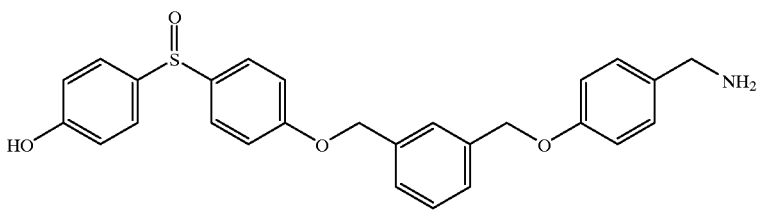 | | |
| hydrochloride | 200–202 | 1.6 |
| 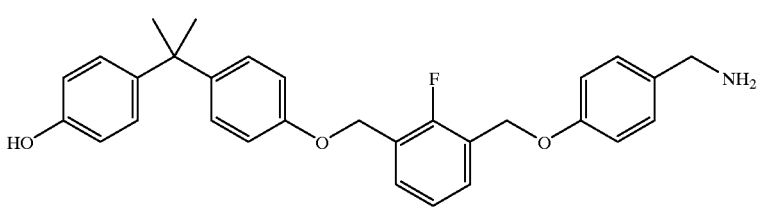 | | |
| hydrochloride | 118–121 | 27.9 |

-continued
| Salt | melting point (° C.) | /K$_i$ (nM) |
|---|---|---|
| 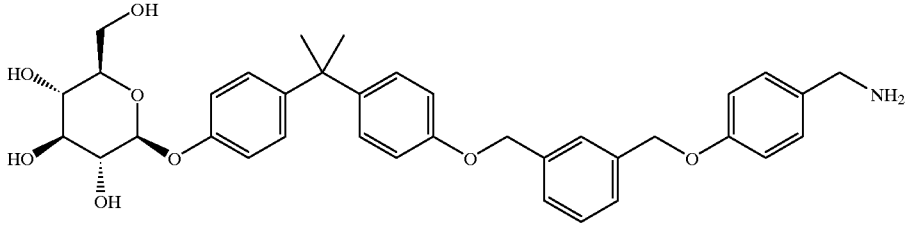 | | |
| hydrochloride | 155 | 0.55 |
| 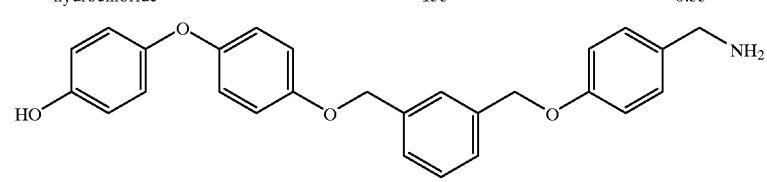 | | |
| | 189–193 | 59.7 |
| 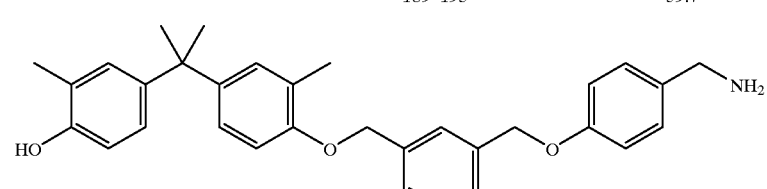 | | |
| hydrochloride | 103–105 | 32.5 |
| 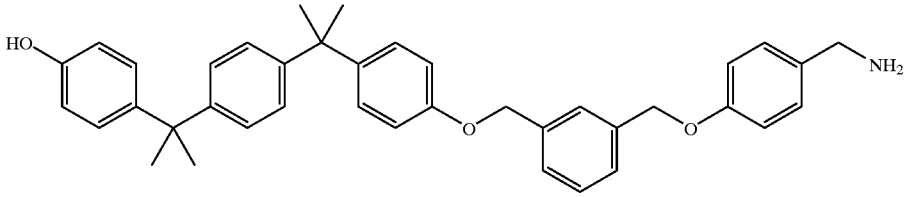 | | |
| hydrochloride | 125–127 | 50.8 |
| 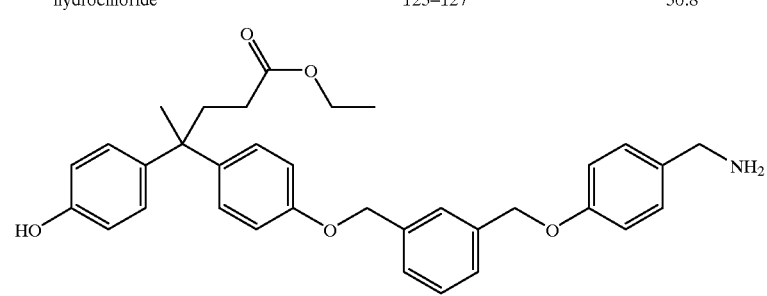 | | |
| fumarate | 143 | 14.9 |
| 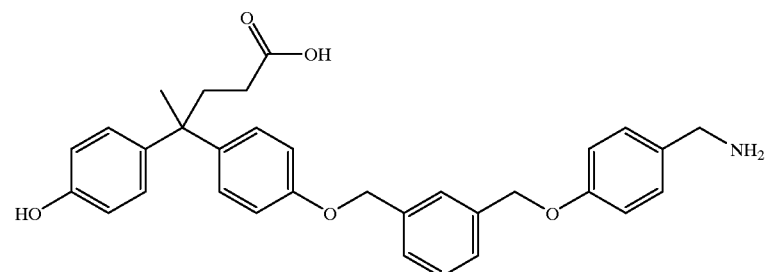 | | |
| | 240 | 0.5 |

-continued
| Salt | melting point (° C.) | /K$_i$ (nM) |
|---|---|---|
| 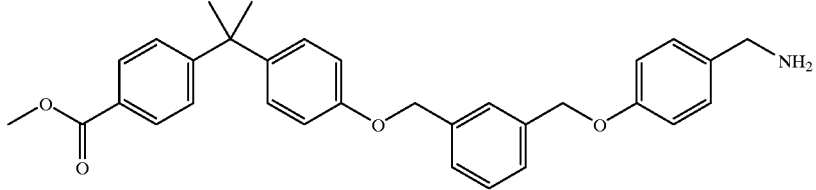 | | |
| methanesulphonate | 175 | 11.4 |
| 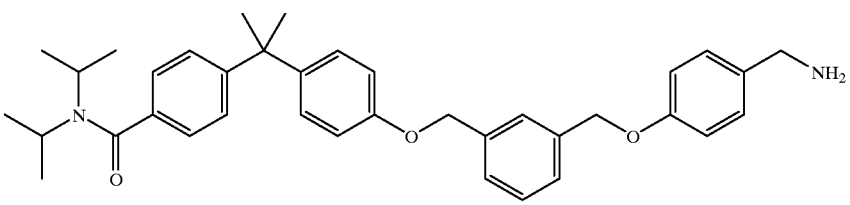 | | |
| fumarate | 177–178 | 13.1 |
| 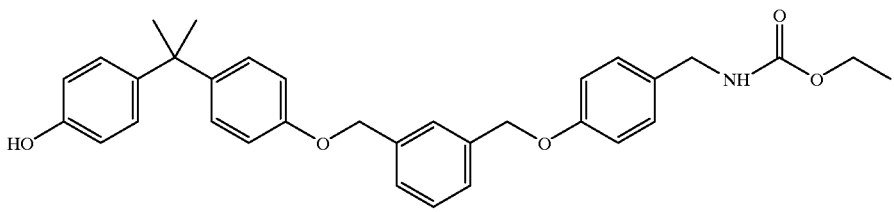 | | |
| | 126–129 | 263 |
| 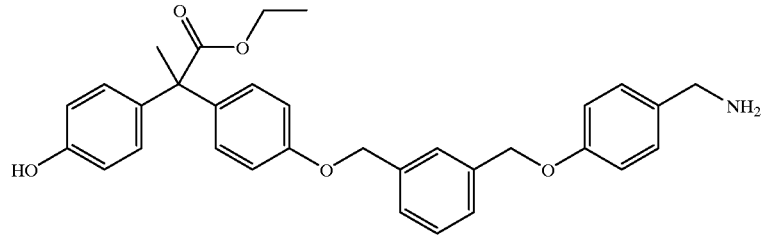 | | |
| fumarate | 120 | 2.85 |
| 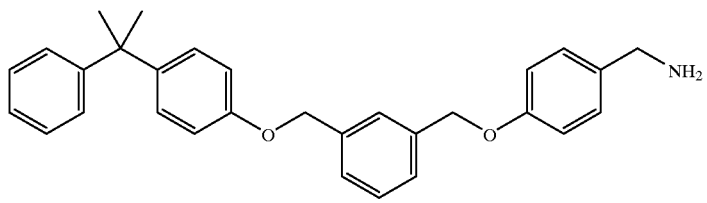 | | |
| hydrochloride | 145 | 30.6 |
| 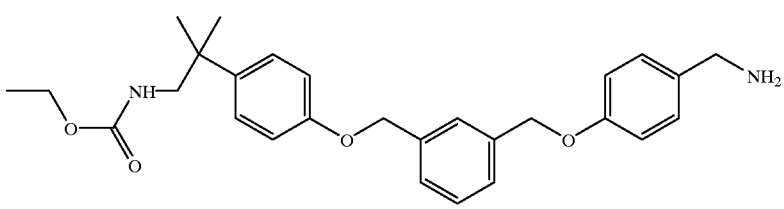 | | |
| fumarate | 158–161 | 4.5 |

| Salt | melting point (° C.) | /K$_i$ (nM) |
|---|---|---|
| fumarate | 208–211 | 67.3 |
| methanesulphonate | 119–121 | 7.5 |
| sulphate | 197–198 | 0.86 |
| | 96–98 | 17.6 |
| | 100–104 | 21.9 |
| HCl | 227–228 | 38.6 |
| | 128–132 | 21.8 |

-continued

| Salt | melting point (° C.) | /K$_i$ (nM) |
|---|---|---|
| | 125 | 10.6 |
| | | |
| | | |
| | | |
| | | |
| methanesulphonate | 175 | 11.4 |
| | 150–155° C. | 2.4 |

What is claimed is:

1. A compound of formula I

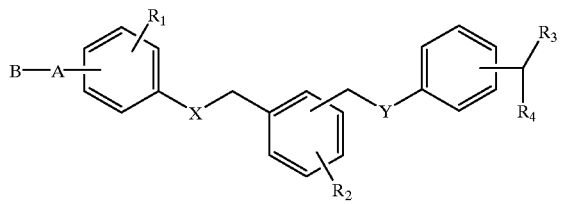

(I)

wherein

X denotes O, NH, N(CH$_3$), or CH$_2$;
Y denotes O, NH, N(CH$_3$), or CH$_2$;
R$_1$ denotes H, F, Cl, Br, I, C$_{1-6}$-alkyl, OH, O—C$_{1-6}$-alkyl, or CF$_3$;
R$_2$ denotes H, F, Cl, Br, I, C$_{1-6}$-alkyl, OH, O—C$_{1-6}$-alkyl, or CF$_3$;
R$_3$ denotes H, NH$_2$, or NHCOR$_5$;
R$_4$ denotes H, CH$_2$NH$_2$, or CH$_2$NHCOR$_5$;
R$_5$ denotes H, C$_{1-6}$-alkyl, phenyl, O—(C$_{1-6}$-alkyl), wherein the phenyl ring is optionally mono- or di-substituted by: F, Cl, Br, I, R$_a$, OR$_a$, or CF$_3$,
R$_a$ denotes H, or C$_{1-6}$-alkyl;
A denotes CR$_6$R$_7$, CO, SO$_x$, or O;
x denotes 0, 1, or 2;
R$_6$ denotes H, C$_{1-4}$-alkyl, C$_{3-6}$-cycloalkyl, —(CH$_2$)$_y$COOR$_8$, CF$_3$, —(CH$_2$)$_y$OR$_8$, or OR$_8$;
y denotes 0, 1, 2, 3, or 4;
R$_7$ denotes H, C$_{1-4}$-alkyl, C$_{3-6}$-cycloalkyl, —(CH$_2$)$_z$COOR$_8$, —(CH$_2$)$_z$OR$_8$, or CF$_3$;
z denotes 0, 1, 2, 3, or 4, wherein R$_6$ and R$_7$ together optionally form a C$_{3-6}$-cycloalkyl ring;
R$_8$ denotes H, or C$_{1-6}$-alkyl;
B denotes C$_{1-6}$-alkyl, Ar, or CONR$_9$R$_{10}$, and, if A represents —C(CH$_3$)$_2$: CH$_2$NR$_9$R$_{10}$, or CH$_2$NR$_9$COR$_{11}$;
Ar denotes phenyl, naphthyl, thienyl, or pyridyl—optionally mono- or di-substituted with R$_{12}$,
R$_9$ denotes H, or C$_{1-6}$-alkyl;
R$_{10}$ denotes H, or C$_{1-6}$-alkyl, wherein R$_9$ and R$_{10}$ together with the nitrogen atom optionally form a ring having 3 to 7 carbon atoms;

$R_{11}$ denotes H, $C_{1-6}$-alkyl, —O—($C_{1-6}$-alkyl), or phenyl;
$R_{12}$ denotes H, $C_{1-6}$-alkyl, O—($C_{1-6}$-alkyl), F, Cl, Br, I, $R_a$, $CF_3$, $CHF_2$, $C(CH_3)_2$-phenylene-OH, $COOR_a$, $CONR_aR_b$, or $OR_c$;
$R_a$ denotes H, or $C_{1-6}$-alkyl;
$R_b$ denotes H, or $C_{1-6}$-alkyl, wherein $R_a$ and $R_b$ together with the nitrogen atom optionally form a ring having 3 to 7 carbon atoms;
$R_c$ denotes H, $C_{1-6}$-alkyl, $COOR_d$, $COR_d$, or a group of formula

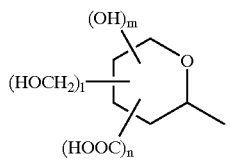

wherein l, m, n each denote 0, 1, 2, 3 or 4 with the proviso that $l+m+n \leq 4$;
$R_d$ denotes $C_{1-6}$-alkyl, or phenyl,
the individual optical isomers thereof, a mixture of the individual enantiomers, a free base thereof such or an acid addition salt thereof with pharmacologically acceptable acids, with the proviso that $R_3$ and $R_4$ together cannot denote hydrogen.

2. The compound according to claim 1, wherein
X denotes O;
Y denotes O;
$R_1$ denotes H, F, Cl, Br, I, $C_{1-6}$-alkyl, OH, O—$C_{1-6}$-alkyl, or $CF_3$;
$R_2$ denotes H, F, Cl, Br, I, $C_{1-6}$-alkyl, OH, O—$C_{1-6}$-alkyl, or $CF_3$;
$R_3$ denotes $NH_2$;
$R_4$ denotes H;
A denotes $CR_6R_7$, or O;
$R_6$ denotes H, $C_{1-4}$-alkyl, or $CF_3$;
$R_7$ denotes H, $C_{1-4}$-alkyl, or $CF_3$, wherein $R_6$ and $R_7$ together optionally form a $C_3$–$C_6$-cycloalkyl ring;
B denotes phenyl, optionally mono- or di-substituted with F, Cl, Br, I, $R_a$, $OR_c$, or $CF_3$;
$R_a$ denotes H, or $C_{1-6}$-alkyl;
$R_c$ denotes H, $C_{1-6}$-alkyl, $COOR_d$, $COR_d$, or a group of formula

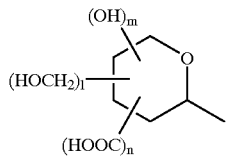

wherein l, m, n each denote 0, 1, 2, 3 or 4 with the proviso that $l+m+n \leq 4$;
$R_d$ denotes $C_{1-6}$-alkyl, or phenyl,
the individual optical isomers thereof, a mixture of the individual enantiomers, a free base thereof or an acid addition salt thereof with pharmacologically acceptable acids.

3. A process for preparing a compound according to claim 1 wherein $R_1$, $R_2$, A, B, X, and Y are as defined in claim 1 and $R_3$, $R_4$, and the carbon atom to which they are attached form an amine group as defined in claim 1, the process comprising:

(a) reacting a benzonitrile derivative of formula IV

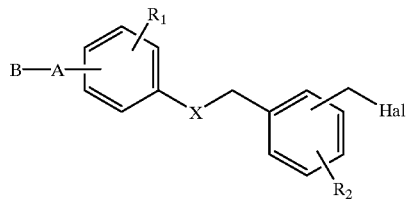

wherein $R_1$, $R_2$, A, B, and X are as defined in claim 1 and Hal represents, in addition to halogen, a nucleofugic leaving group, with a phenol of formula III

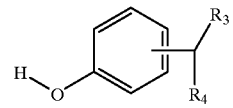

wherein $R_3$ and $R_4$ are as defined in claim 1, in the presence of a base in a polar solvent; and (b) isolating the reaction product.

4. The process according to claim 3, wherein the nucleofugic leaving group is chlorine, alkyl sulphonate, or aryl sulphonate.

5. The process according to claim 3, wherein the base is a hydroxide, alkoxide, or a carbonate of an alkali or alkaline earth metal.

6. The process according to claim 3, wherein the polar solvent is dimethylformamide, acetonitrile ethanol, or a mixture thereof.

7. A process for preparing a compound according to claim 1, wherein $R_1$, $R_2$, A, B, X, and Y are defined in claim 1 and $R_3$, $R_4$, and the carbon atom to which they are attached form an amine as defined in claim 1, the process comprising:
reducing a benzonitrile derivative of formula IV

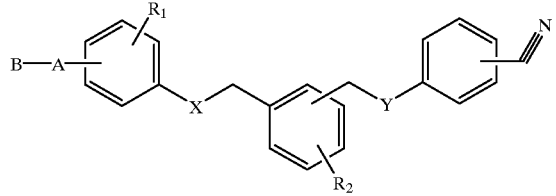

at a temperature of about 0° C. to about 100° C. to form the corresponding amine of formula I of claim 1.

8. The process according to claim 7, wherein the reduction is by hydrogenation in a solvent chosen from methanol, ethanol or a higher alcohol, DMF, or water in the presence of a catalyst chosen from Raney nickel, Pd/C, or platinum, at a hydrogen pressure of greater than about 760 torr.

9. The process according to claim 7, wherein the reduction is accomplished with complex hydrides chosen from the group $NaBH_4$, $Ca(BH_4)_2$, $LiAlH_4$, or other aluminum or boron hydrides.

10. A pharmaceutical composition of matter comprising a compound according to claim 1.

11. A method of treating disease in a warm-blooded animal which disease is responsive to compounds with LTB$_4$-antagonistic activity, the method comprising administering to an animal in need of such treatment a therapeutically effective amount of a compound according to claim 1.

12. A method of treating arthritis, asthma, chronic obstructive lung disease, psoriasis, ulcerative colitis, gastropathy or enteropathy induced by non-steroidal anti-inflammatories, cystic fibrosis, Alzheimer's disease, shock, reperfusion damage/ischaemias, atherosclerosis, or multiple sclerosis in a warm-blooded animal, the method comprising treating the animal with a therapeutically effective amount of a compound according to claim 1.

* * * * *